United States Patent [19]

Shroot et al.

[11] Patent Number: 5,073,361
[45] Date of Patent: Dec. 17, 1991

[54] COMPOUND MARKED WITH TRITIUM, ITS PREPARATION AND ITS USE IN THE LOCATION OF NUCLEAR RECEPTORS OF RETINOIDS

[75] Inventors: Braham Shroot; Michel Darmon, both of Antibes, France

[73] Assignee: Centre International De Recherches Dermatologiques Galderma (CIRD Galderma), Valbonne, France

[21] Appl. No.: 553,812

[22] Filed: Jul. 19, 1990

[30] Foreign Application Priority Data

Jul. 20, 1989 [FR] France .................................. 89 09778

[51] Int. Cl.$^5$ ........................ A61K 49/02; C07C 63/34
[52] U.S. Cl. ...................................... 424/1.1; 562/467
[58] Field of Search ......................... 562/467; 424/1.1

[56] References Cited

FOREIGN PATENT DOCUMENTS 0199636 10/1986 European Pat. Off. .
2194535 3/1988 United Kingdom .

OTHER PUBLICATIONS

French Search Report of FR 89 09778.

Primary Examiner—John S. Maples
Attorney, Agent, or Firm—Cushman, Darby & Cushman

[57] ABSTRACT

6-[3-(1-adamantyl)-4-methoxyphenyl]-2-naphthoic acid marked with tritium; its preparation; and its use as a radioactive marker, in the titration of nuclear receptors of retinoids in the presence of contaminating CRABP, or in the measurement of the affinity of retinoids for these nuclear receptors.

6 Claims, 2 Drawing Sheets

COMPOUND MARKED WITH TRITIUM, ITS PREPARATION AND ITS USE IN THE LOCATION OF NUCLEAR RECEPTORS OF RETINOIDS

The present invention relates to a new compound, marked with tritium, which is related to retinoids, to its preparation and to its use principally in the determination of the affinity of retinoids for their nuclear receptors and/or in the determination of the cellular content of nuclear receptors. The peculiarity and advantage of this compound is its absence of affinity for the cytosolic binding protein (CRABP).

It is known that retinoids constitute a known class of compounds which act, in particular, on the proliferation and differentiation of numerous types of cells; see, for example, B. A. Pawson et al, Journal of Medicinal Chemistry, Vol. 25, No. 11, pages 1269–1277 (1982).

Retinoids have been used, in particular, in the treatment of various dermatological disorders in which an irregularity of the mechanism for control of the proliferation and differentiation of the epidermal cells is involved; see for example, the work "Update: Dermatology in General Medicine", edited by Thomas B. Fitzpatrick et al (MacGraw-Hill Book Company), published in 1983, and particularly the chapter by D. B. Windhorst et al, The Retinoids, pages 226–237.

The method of action of retinoids is similar to that of steroids and other effectors interacting with nuclear receptor (Chytil & Ong. Proc. Fed. Am. Soc. Exp. Biol., Vol. 38, 2510–514 (1979). Retinoic acid nuclear receptors (RARs) have been isolated (Daly & Redfern, Eur. J. Biochem., Vol. 168, 133–139, 1987) and the corresponding complementary DNAs have been cloned and sequenced (Petkovich et al, Nature, Vol. 330, 444–450, 1987); (Brand et al., Nature, Vol. 332, 850–853, 1988). To date, two receptors have been described in man, RAR $\alpha$ (462 residues) and RAR$\beta$ (448 residues). In addition it has been shown that there exists in cytosol a binding protein, known as CRABP (cellular retinoic acid binding protein), but its role is little known.

The determination of the affinity of a retinoid for the RARs comprises a particularly interesting method of potential biological evaluation of said retinoid. However, the presence of CRABP can hinder this affinity determination for RARs in the case of classic retinoids.

Several experimental methods enable the determination of the affinity of a ligand for its receptors or binding proteins. In particular, a direct method can be used if the ligand under consideration is radioactively marked, or even by competition with a radioactive ligand if the ligand under consideration is not radioactively marked.

A good radioactive ligand must, on the one hand, have a high affinity for its receptors and, on the other hand, have low fixing on any other molecule. In addition, it must be sufficiently stable to be useful in practice.

In the case of retinoid acids, the radioactive ligand generally used is most often tritiated retinoic acid, either in the 2-position (J. Labelled Compounds and Radiopharmaceuticals XVIII, p. 1099 (1980)) or in the 4-position (German Patent Application No. 3.142.945).

Retinoic acid certainly has an excellent affinity for RARs, with low non-specific fixing, but the molecule has the disadvantage of becoming rapidly degraded by radiolysis, oxidation and photolysis. On the other hand, retinoic acid is also capable of being fixed on CRABP.

It has now been discovered that tritiated 6-[3-(1-adamantyl)-4-methoxyphenyl]-2-naphthoic acid constitutes a new radioactive ligand which has an excellent affinity for RARs, but has no affinity for CRABP. In addition, this new ligand is very stable and can be obtained with high specific activity, which makes it particularly useful for the measurement of the affinity of retinoids for RARs and particularly under conditions where CRABP is also present.

The present invention therefore relates to 6-[3(1-adamantyl)-4-methoxyphenyl]-2-naphthoic acid marked with tritium, and principally in the 5-position of the methoxyphenyl adamantyl group and in the 5-position of the naphthoic moiety.

The present invention also principally relates to a new radioactive ligand, such as defined above, having a specific activity greater than 10 Ci/mmole (about 370 GBq/mmole) and preferably at least equal to 30 Ci/mmole, or about 100 GBq/mmole.

The present invention also relates to a method for the preparation of the new radioactive ligand, such as defined above. This method is principally characterized by the fact that a multihalogenated alkyl ester of 6-[3-(1-adamantyl)-4-methoxyphenyl]-2-naphthoic acid is prepared which is then submitted to the action of a tritiated reducing agent, then to the action of a saponification agent.

The halogen, preferably, is bromine.

The reducing agent is, principally, tritium. The reduction reaction is carried out in accordance with known methods, for example, in the presence of a catalyst, such as palladium, at ambient temperature.

The tritiated alkyl ester obtained after the reduction is then saponified in accordance with conventional methods, for example, by an alkaline base such as soda, in a methanolic medium.

The halogenated derivative used as the starting product is principally a dihalogenated derivative, preferably a brominated derivative. The dihalogenated derivative is, in particular, the derivative halogenated in the 5-position of the adamantyl methoxyphenyl group and in the 5-position of the naphthoic moiety. The alkyl ester employed is, preferably, a lower alkyl ester (1–6 carbon atoms) such as the methyl ester.

The multihalogenated alkyl ester of 6-[3-(1-adamantyl)-4-methoxyphenyl]-2-naphthoic acid can itself be prepared from the alkyl ester of 6-[3-(1-adamantyl)-4-methoxyphenyl]-2-naphthoic acid by the action of a halogenation agent (in particular a bromination agent). For example, the brominated derivative can be obtained by the action of bromine in dichloromethane at ambient temperature and under a nitrogen atmosphere.

6-[3-(1-adamantyl)-4-methoxyphenyl]-2-naphthoic acid is a known product (hereinafter called Compound I), as well as its esters. It can be obtained in accordance with the process described in European patent application No. 86.400785 (199.636).

The present invention also relates to, as an intermediate product obtained in the process described above, 6-[3-(1-adamantyl)-4-methoxy-5-halogenophenyl]-5-halogeno-2-naphthoic acid, and in particular the dibrominated derivative.

The present invention also relates to the use of tritiated 6-[3-(1-adamantyl)-4-methoxyphenyl]-2-naphthoic acid as a radioactive marker, principally for the measurement of the affinity of substances such as retinoids for RARs, in accordance with a competition method.

The radioactive marker of the present invention can also be used:

in the characterization of antibodies against Compound I, these antibodies (obtained in accordance with conventional methods for obtaining anti-haptene antibodies) themselves being useful in the determination of the amount of Compound I fixed or not on RARs; one can jointly use Compound I and the said antibodies to effect a radioimmunodosage;

in the study of the distribution in vivo as well as cellular and subcellular of Compound I, without interference with CRABP.

The radioactive marker of the present invention can also be employed in the study of the mechanism of intracellular action and of the general metabolism of Compound I in vivo and in the cells and cellular extracts.

These uses are operated in accordance with conventional methods.

The following non-limiting example illustrates the present invention.

EXAMPLE 1

6-[3-(1-adamantyl)-4-methoxyphenyl]-2-naphthoic acid marked with tritium (a) A mixture of the methyl ester corresponding to the cited acid (1 g; 2.4 mmoles) and 4.5 ml of bromine in 30 ml of dichloromethane is stirred for 24 hours.

The mixture is added to 50 ml of water, then extracted with dichloromethane (150 ml).

The organic phase is separated, washed with water, then with a saturated solution of sodium bicarbonate and finally with sodium thiosulfate.

It is then dried on anhydrous magnesium sulfate and the solvent is evaporated under reduced pressure.

1.24 g of an orange yellow solid corresponding to a dibrominated product according to its mass spectrum are obtained. The position of the bromine atoms is confirmed by analysis of the NMR spectrum of the proton, in comparison with the NMR spectrum of the non-brominated derivative. The product obtained is the methyl ester of 6-[3-(1-adamantyl)-4-methoxy-5-bromophenyl]-5-bromo-2-naphthoic acid.

(b) The brominated product obtained is then tritiated in the following manner:

10 mg of the dibrominated compound are dissolved in 2 ml of ethanol and 1 ml of THF. 17 μl of triethylamine and 14 mg of palladium on charcoal (10%) are added. The medium is stirred for 2 hours under a tritium atmosphere and the catalyst is removed by filtration. Then the solvent is removed by evaporation under reduced pressure. The residue is taken up 3 times with methanol. Thereafter the solvent is removed by evaporation under reduced pressure.

The resulting residue is dissolved in the minimum of tetrahydrofuran and purified by chromatography on a silica plate, the eluant being a 9:1 mixture of dichloromethane and methanol. The fluorescent band under UV radiation at 320 nm is collected.

There is thus obtained the methyl ester of 6-[3-(1-adamantyl)-4-methoxyphenyl]-2-naphthoic acid (96 mCi) marked with tritium in position 5 of the methoxy phenyl adamantyl group and in position 5 of the naphthoic group.

(c) The preceding tritiated product (96 mCi) is dissolved in 5 ml of methanol. 6 μl of 5N soda are added and the resulting mixture is heated at reflux for 3 hours, cooled, acidified using 2 ml of 6N HCl and then extracted with 50 ml of ethyl ether.

The ether phase is decanted, washed with water, dried on anhydrous magnesium sulfate and the solvents evaporated under reduced pressure. The resulting residue is dissolved in 2 ml of ether and purified by high performance liquid chromatography (eluant: 100% ethyl ether). 83 mCi of this product is obtained as a saponification yield of 86%.

The final product is dissolved in 100 ml of methanol. Its purity is verified by thin layer chromatography (silica, above eluant). A single spot is apparent under UV radiation (254 and 3666 nm) and during beta counting.

By HPLC (inverse phase, ZORBAX ODS column, eluant: 43/36/21/0.2 acetonitrile/THF/water/trifluoroacetic acid) a single peak is detected by UV (320 nm) and by beta detection (continuous liquid scintillation).

The specific activity determined by UV spectrophotometry, then beta counting, is 33.0 Ci/mmole.

The total activity obtained, measured by counting with a liquid scintillator, is 83 mCi.

Characteristics of the Fixing of the Compound of Example 1 on Nuclear Receptors RARs Cultures of F9 cells of murin embryonic carcinoma (normally four 90 mm dishes containing in total $4-7 \times 10^7$ cells per incubation condition) were washed once with PBS (saline phosphate buffer) and incubated for 3 hours in a medium, without serum, supplemented with the marked retinoic homolog (to verify the specifity). The cells were then detached with a trypsin-EDTA mixture and numbered with a Burker hemocytometer. The nucleosol containing RARs was extracted from the purified nuclei using the method described by Daly and Redfern (1987) (that is, after treatment using DNAse and 0.6M NaCl), and analyzed using high performance exclusion chromatography (HPSEC). 50 μl of marked extract were injected on a $9 \times 250$ mm GF 250 column (Dupont de Nemours). The elution was carried out in a buffer 0.3M $KH_2PO_4$, pH 7.8 at a rate of 1 ml/min. The protein content was followed by measuring the optical density at 280 nm. 28 fractions of 0.3 ml each were collected and counted in Picofluor (Packard) scintillating agent. For each retinoid concentration, the number of bonded molecules was determined using the surface of the radioactivity peak and the calculated concentration of demi-saturation (C50). The molecular weight calibration of the column was carried out using human albumin (67kDa) ovalbumin (45kDa) and myoglobin (16.8kDa). The dose-response curves and the competition curves were analyzed on a computer through non-linear regression using the various forms of the Clark equation.

FIG. 1 (A and B) represents the HPSEC profile in the detection of retinoic acid nuclear receptors (RARs) by the compound of Example 1 in a fraction of approximately 45kDa in the nucleosol of F9 cells, in comparison with tritiated retinoic acid.

The F9 cells incubated with 20 nM of tritiated retinoic acid (specific activity, 52.5 Ci/mmole) (1A) in the absence (□—□) or in the presence (○—○) of 100 times more of cold retinoic acid, or with 20 nM of the tritiated compound of Example 1 (1B) in the absence (□—□) or presence (○—○) of 1000 times more of cold compound I. The quantity of ligand linked to the RARs is expressed in dpm (disintegration/minute).

When the above-described method is used and the F9 cells are incubated with the compound of Example 1 at a concentration of 20 nM, a single radioactivity peak is observed in the nuclear extract (FIG. 1B). The molecular weight corresponding to the average fraction of the peak is approximately 45kDa, a number close to the molecular weight of human RARs, as has been calculated from the sequence of their DNAc (Petkovich et al, 1987; Brand et al, 1988), and is compatible with the 4s sedimentation coefficient of murin receptors (Daly & Redfern), 1987). The fixing is specific since it is abolished when the cells are co-incubated with an excess of 1000 times of the cold compound I (FIG. 1B).

On the other hand, by transfection of cellular stock not containing retinoid receptors with expression vectors coding separately for each retinoid receptor, it is possible to isolate cellular extracts containing each receptor and to carry out a binding test using the protocol described above. In this manner, the affinity of the compound of Example 1 can be determined for each retinoid receptor.

Comparison with the Fixing of Tritiated Retinoic Acid on the Nuclear Receptors RARs On FIG. 1A it can be noted that the radioactive peak elutes at the same position as with the compound of Example 1. On the other hand, this fixing is also inhibited by an excess of 100 times of cold retinoic acid.

If the HPSEC results are standardized as a function of the number of cells, that is, by expressing them by molecules of ligand fixed to the RARs per cell, the compound of Example 1 and retinoic acid give a peak with the same surface corresponding to approximately 4,000 molecules per cell.

Characteristics of Fixing the Compound of Example 1 on CRABP Binding Protein

The results concerning the fixing of compound I and retinoic acid on CRABP are shown in FIG. 2A and FIG. 2B. The direct fixing of increasing concentrations of the compound of Example 1 (FIG. 2B, bottom curve) and retinoic acid (FIG. 2A, top curve) to rat testicle cytosol containing CRABP in the absence (●—●) or in the presence of 1000 nM of cold homolog ligand (□—□) was studied. The difference (■—■) represents the specific bond.

The fixing of the claimed compound on CRABP has been compared to that of retinoic acid. The total fixing non-specific +specific (●—●) is obtained by incubation of increasing concentrations (up to a maximum of 125 nM) of the claimed compound with a constant quantity (0.3 ml) of a rat testicle homogenate (CRABP-rich organ). The non-specific fixing of the tritiated compound is determined in parallel, by measuring the fixing with increasing concentrations of the radioactive ligand in the presence of a large excess (1 μm) of cold homolog ligand (□—□). An incubation time of two hours is necessary for the establishment of balanced conditions.

Once the balance is achieved, the tritiated CRABP-ligand complex is separated from the non-bonded ligand by filtration on a Sephadex G25 exclusion gel column (B10-Rad econo columns, 0.5×20 cm): the complex is eluted (elution peak at 2.5 ml), while the non-bonded ligand is retained in totality on the column. The result is total separation between the bonded and non-bonded product. The elution is done directly in scintillation tubes and the radioactivity is measured by counting.

On FIG. 2B, at the bottom, it can be noted that the compound claimed exhibits no specific fixing on CRABP, the specific fixing curves and non-specific fixing curves being totally superimposable.

Comparison with Tritiated Retinoic Acid

Under these same conditions, the fixing of retinoic acid on CRABP (FIG. 2A, at the top) can be studied. On FIGS. 2A and 2B the abscissa represents the concentrations of free retinoic acid and the ordinate represents the concentrations at equilibrium of the bonded ligand-protein complex.

The difference between the total fixing curve (●—●) and non-specific fixing (□—□) gives the specific fixing curve (■—■). Analysis of this curve provides the dissociation constant at equilibrium (Kd) which is the concentration of the product required for 50% saturation of CRABP. This constant is a measurement of the affinity of the ligand for its bonding protein, Kd being inversely proportional to affinity (the smaller the Kd, the greater the affinity). This analysis gives for retinoic acid a Kd value of 2 nm. The specific fixing is saturable and reversible. Non-specific fixing is linear and non-saturable in the range of concentrations employed, and represents less than 20 percent of the total fixing.

What is claimed is:

1. 6-[3-(1-adamantyl)-4-methoxyphenyl]-2-naphthoic acid marked with tritium.

2. The tritiated 6-[3-(1-adamantyl)-4-methoxyphenyl]-2-naphthoic acid of claim 1, marked in position 5 of the adamantyl methoxyphenyl group and in position 5 of the naphthoic moiety.

3. The tritiated 6-[3-(1-adamantyl)-4-methoxyphenyl]-2-naphthoic acid of claim 1 having a specific activity of at least 370 GBq/mmole.

4. The tritiated 6-[3-(1-adamantyl)-4-methoxyphenyl]-2-naphthoic acid of claim 1 having a specific activity of at least 1100 GBq/mmole.

5. In a method, using a radioactive marker, to study in vivo, cellular and subcellular distribution of 6-[3-(1-adamantyl)-4-methoxyphenyl]-2-naphthoic acid, without interference with CRABP, the improvement comprising, as the radioactive marker, tritiated 6-[3-(1-adamantyl)-4-methoxyphenyl]-2-naphthoic acid.

6. In a method, using a radioactive marker, to study the metabolism of 6-[3-(1-adamantyl)-4-methoxyphenyl]-2-naphthoic acid in vivo and in cells and cellular extracts, the improvement comprising, as the radioactive marker, tritiated 6-[3-(1-adamantyl)-4-methoxyphenyl]-2-naphthoic acid.

* * * * *

UNITED STATES PATENT AND TRADEMARK OFFICE
CERTIFICATE OF CORRECTION

PATENT NO. : 5,073,361
DATED : December 17, 1991
INVENTOR(S) : SHROOT, Braham; DARMON, Michel It is certified that error appears in the above-identified patent and that said Letters Patent is hereby corrected as shown below: Column 3, after line 21, please insert the following:

--BRIEF DESCRIPTION OF THE FIGURES

Figure 1 (A and B) represents the HPSEC profile in the detection of retinoic acid nuclear receptors (RARs) by the compound of Example 1 in a fraction of approximately 45kDa in the nucleosol of F9 cells, in comparison with tritiated retinoic acid. The $F_9$ cells incubated with 20 nM of tritiated retinoic acid (specific activity, 52.5 Ci/mmole) (1A) in the absence (◘ - ◻ ) or in the presence (O - O) of 100 times more of cold retinoic acid, or with 20 nM of the tritiated compound of Example 1 (1B) in the absence (◻ - ◘ ) or presence (O - O) of 1000 times more of cold compound I. The quantity of ligand linked to the RARs is expressed in dpm (disintegration/minute).

Fig. 2 (A and B) represents the results concerning the fixing of compound I and retinoic acid on CRABP. The direct fixing of increasing concentrations of the compound of Example 1 (Fig. 2, bottom curve) and retinoic acid (Fig. 2, top curve) to rat testicle cytosol containing CRABP in the absence (O - O) or in the presence of 1000 nM of cold homolog ligand (◻ - ◻ ) was studied. The difference (◘ - ◻ ) represents the specific bond.--

Signed and Sealed this

Third Day of August, 1993

*Attest:*

MICHAEL K. KIRK

Figures 1A, 1B:
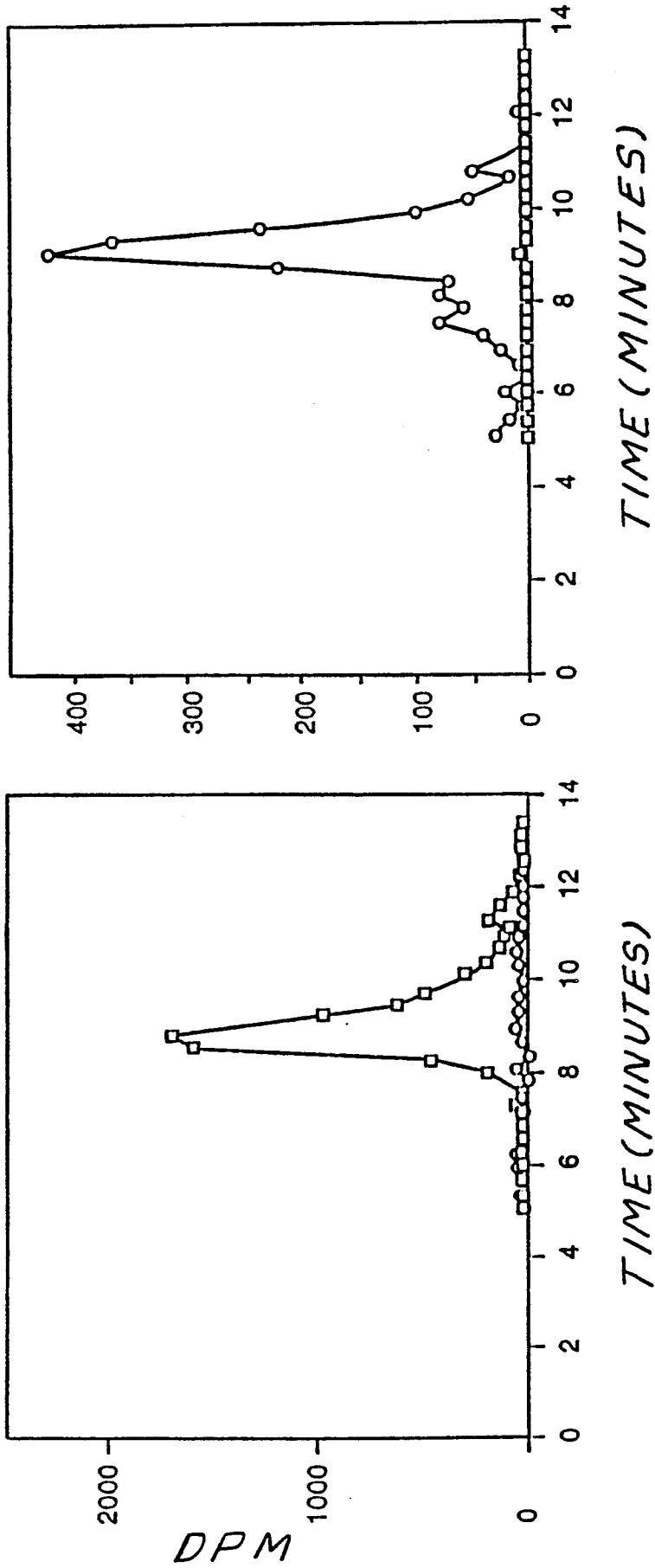
Figure 1.
Figure 2A:
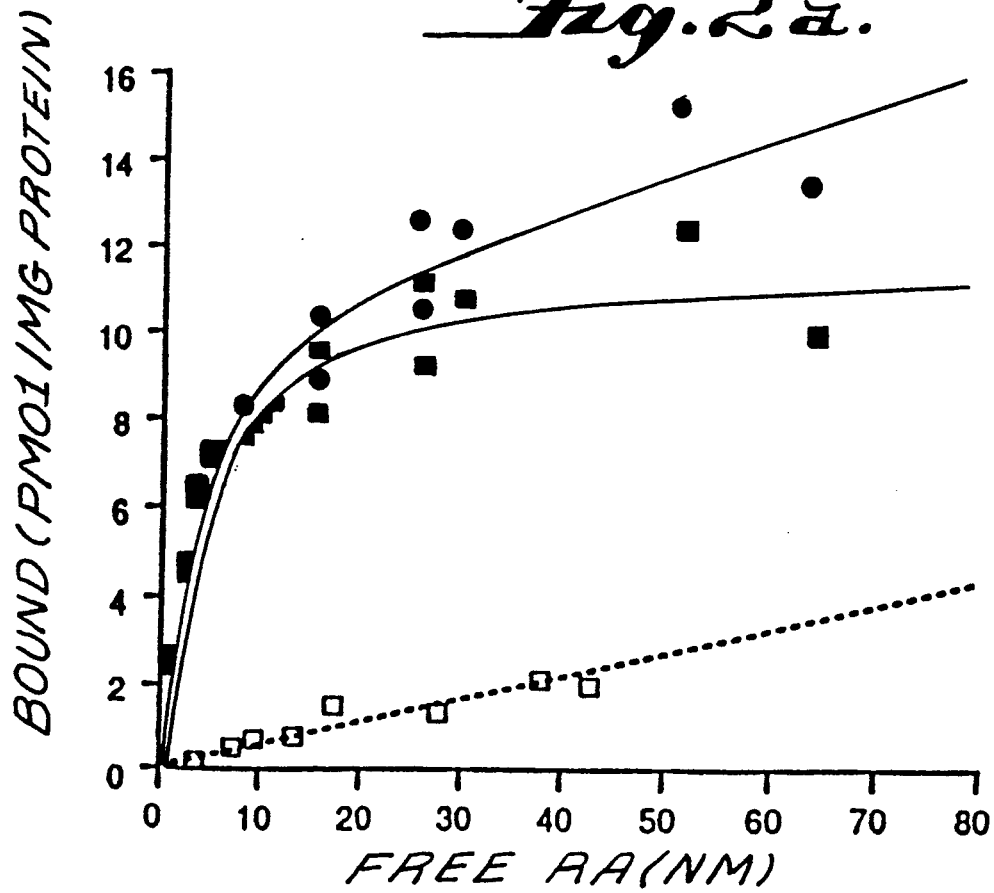
Figure 2.
Figure 2B:
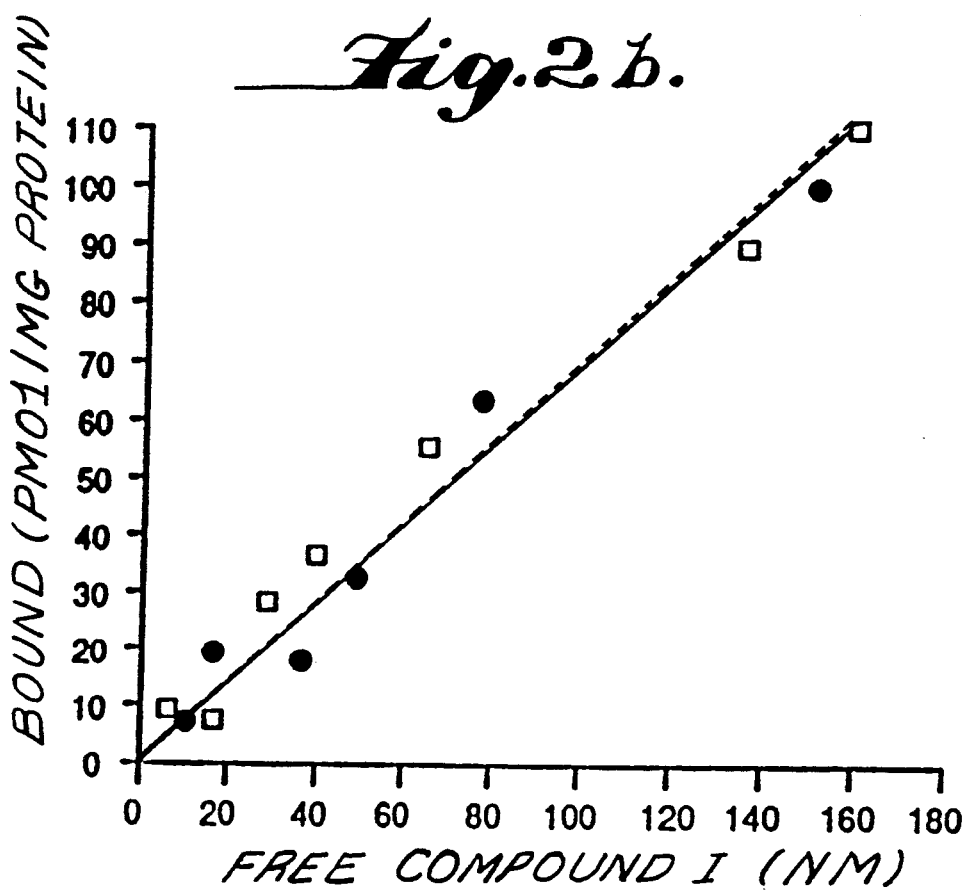

*Attesting Officer*    Acting Commissioner of Patents and Trademarks